United States Patent [19]

Dulapa

[11] Patent Number: 4,549,210
[45] Date of Patent: Oct. 22, 1985

[54] HOLE-FILL TECHNIQUE FOR DIAGNOSTIC ULTRASOUND IMAGING SYSTEMS

[75] Inventor: Mark J. Dulapa, Denver, Colo.

[73] Assignee: Technicare Corporation, Solon, Ohio

[21] Appl. No.: 536,415

[22] Filed: Sep. 27, 1983

[30] Foreign Application Priority Data

Oct. 1, 1982 [UK] United Kingdom ............ 8228094

[51] Int. Cl.⁴ ............................................... H04N 5/30
[52] U.S. Cl. ..................... 358/112; 128/660; 364/577; 73/607
[58] Field of Search ........................ 358/112, 138, 140; 364/514, 577; 343/5 SC; 73/606, 607; 128/660; 371/31, 65; 455/303, 304, 305

[56] References Cited

U.S. PATENT DOCUMENTS

| | | | |
|---|---|---|---|
| 4,167,753 | 9/1979 | Lynk | 358/112 X |
| 4,212,072 | 7/1980 | Huelsman et al. | 358/112 X |
| 4,310,853 | 1/1982 | Madson | 358/112 X |
| 4,310,907 | 1/1982 | Tachita et al. | 358/112 X |
| 4,381,787 | 5/1983 | Hottinger | 128/660 |
| 4,386,528 | 6/1983 | Engle | 358/112 X |
| 4,448,201 | 5/1984 | Matsumoto | 358/112 X |
| 4,468,747 | 8/1984 | Leavitt et al. | 358/112 X |

*Primary Examiner*—Howard W. Britton
*Assistant Examiner*—Victor R. Kostak
*Attorney, Agent, or Firm*—W. Brinton Yorks, Jr.

[57] ABSTRACT

In an ultrasonic scanning and display system, lines of pixel values to be displayed comprise pixel values resulting from reception of echoes separated by pixels for which no echo information was received. The "holes" between pixels representing echo information are selectively filled in with interpolated values when the length of the sequence of holes is less than a selected number, and sequence of holes greater than the selected number are blanked for display. This arrangement permits the system operator to select the degree to which the display contains interpolated information.

8 Claims, 12 Drawing Figures

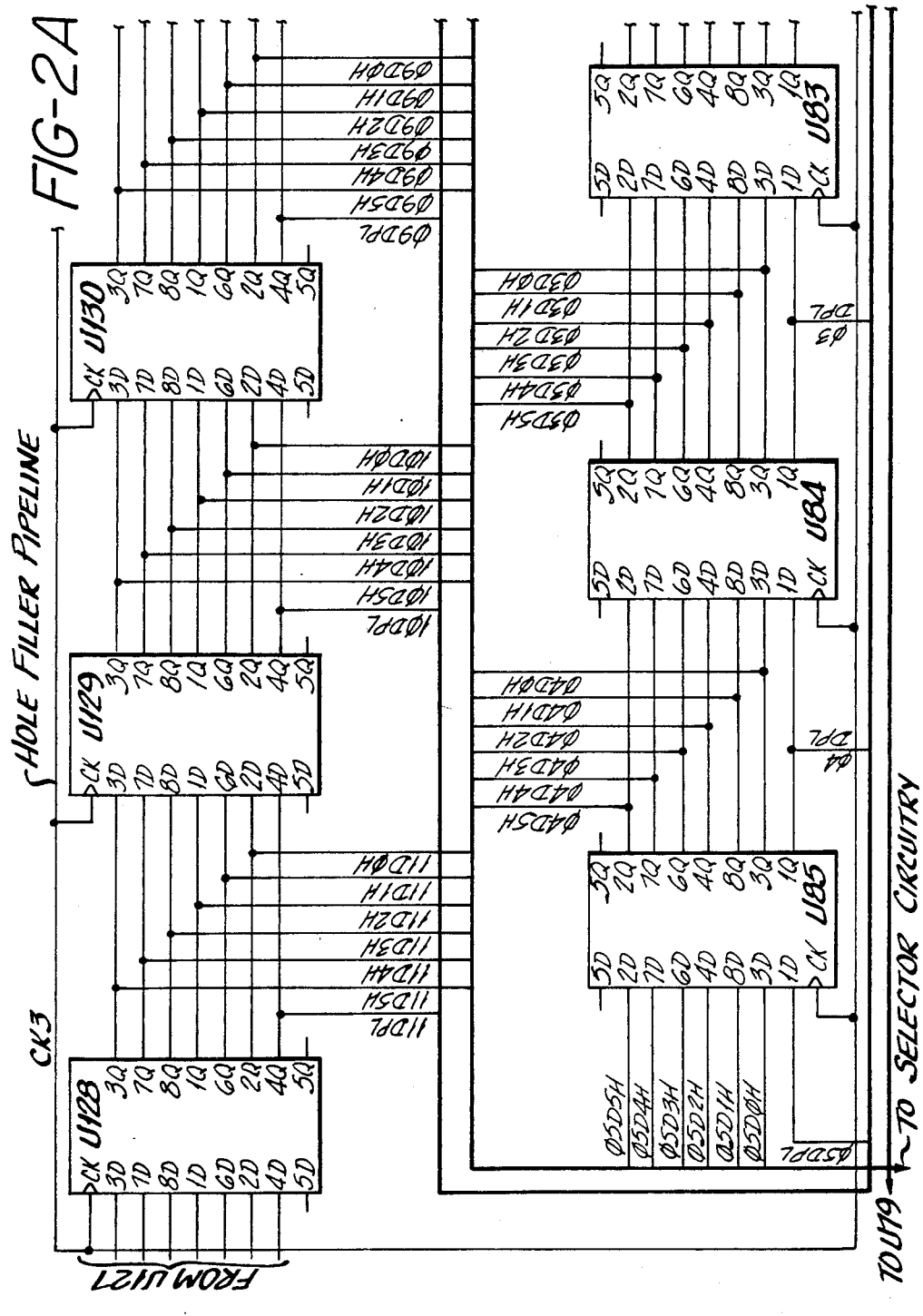

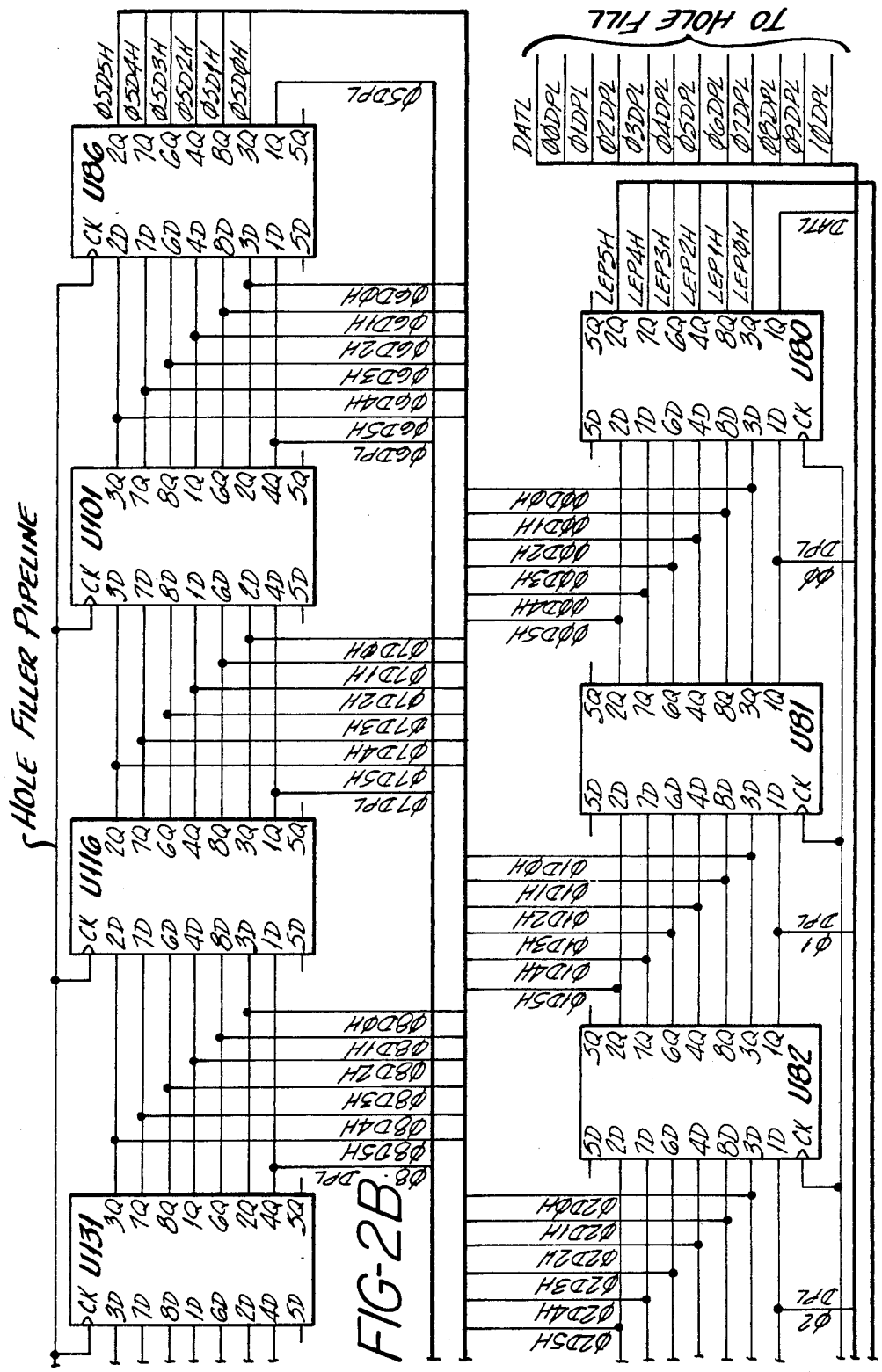

HOLE-FILL TECHNIQUE FOR DIAGNOSTIC ULTRASOUND IMAGING SYSTEMS

This invention relates to techniques for interpolating data values for ultrasonic imaging systems and, in particular, to a technique for selectively filling in "holes" in acquired ultrasound data up to a predetermined maximal size.

U.S. Pat. No. 4,381,787, entitled "ULTRASOUND IMAGING SYSTEM COMBINING STATIC B-SCAN AND REAL-TIME SECTOR SCANNING CAPABILITY", by Charles F. Hottinger describes a system which is capable of developing images using either a real-time sector scanning head or a static B-scan probe. Preferred techniques for use entail utilization of the real-time sector scanner first for surveying and coarse examination purposes. Use of the sector scanner enables the operator to quickly locate and identify particular tissue areas of interest about which more detailed information is desired. The sector scanner information is generally displayed as a sector or a trapezoidal segment of a sector, but involves disadvantages chiefly due to the limited field of view, low line density in the image, and the lack of precise coordination of the image with positional information about the tissue.

Once a tissue region of interest has been localized, a static B-scan may be conducted for detailed evaluation and hard copy reproduction with respect to any lesions or the like first located utilizing the sector scanner. The static B-scan image is preferable for detailed analysis because it is characterized by a wide field of view and high line density. Reliable tissue diagnoses may thereby be obtained.

In both scanning techniques the echo information received by the probes is stored and arranged in an intensity-modulated array of picture elements or pixels. The ultrasonic beams transmitted into the tissue for echoing generally do not correlate one-to-one with each displayed pixel due to the speed at which the probe is moved across the patient and divergence of the beams of ultrasonic energy; rather, a number of lines of data points are recorded from the echo information having regions between them for which no echo information has been received. This is particularly true at increasing tissue depths, where the transmitted beams tend to diverge widely. Accordingly, pixels for which no echo information has been received may be filled in by an interpolation technique using adjacent known data values.

In accordance with the principles of the present invention, pixels for which no information has been received, termed "holes", are filled in by different, selectable techniques which determine the permissible degree of interpolation. In a preferred embodiment of the present invention, the number of pixels comprising holes to be filled in between known data points is selected over a range of one to thirteen. If the number of holes exceeds the selected number, the line is blanked on the displayed image. Since the sector scanner is to be used for coarse examination, a greater number of holes will generally be permitted to be filled in during this mode of operation than during the static B-scan mode, when more precise, reliable displays are desired.

In the Drawings:

FIGS. 2A and 2B illustrate a shift register containing a sequence of image pixels;

Figure 6:
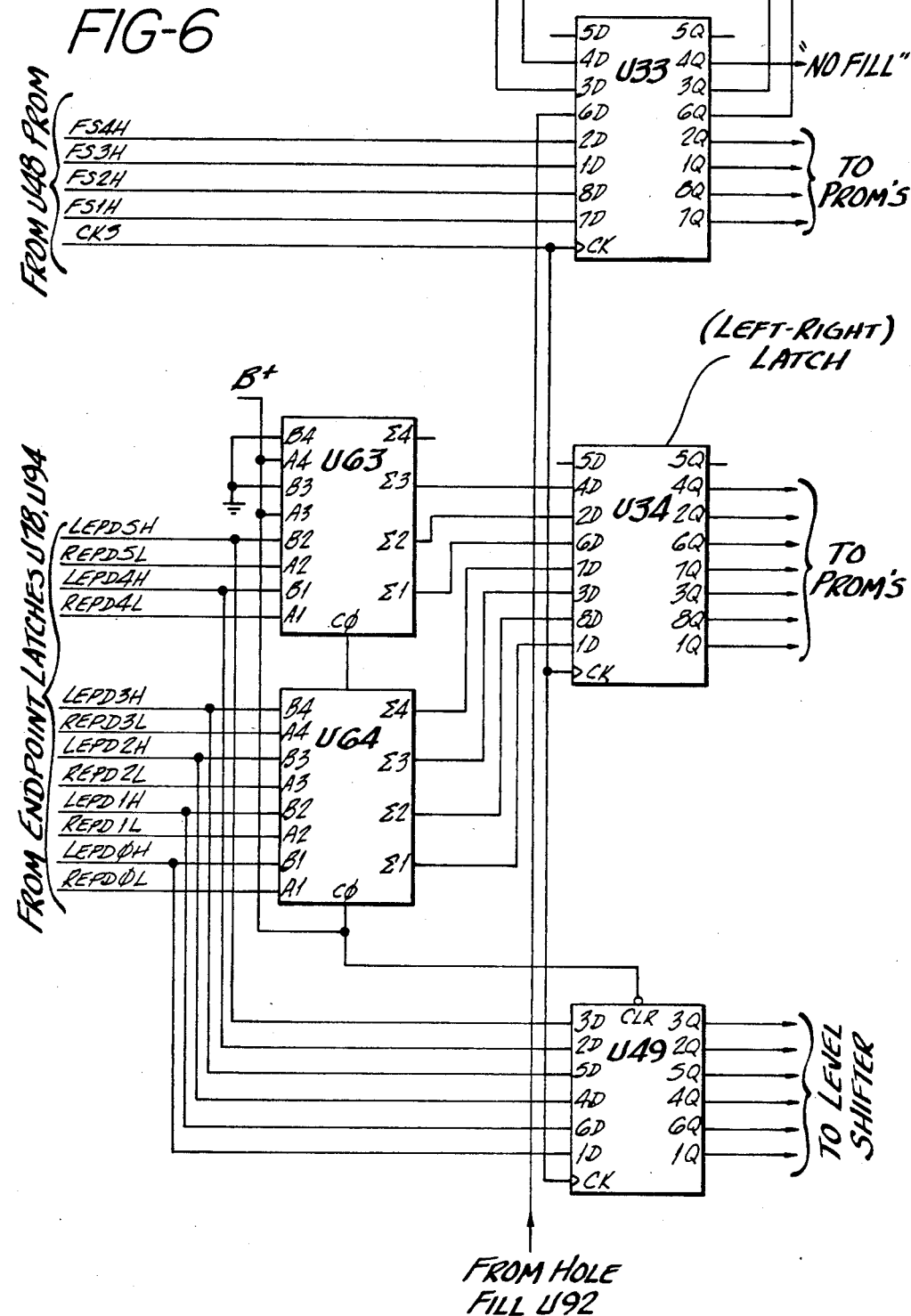
Figure 7:
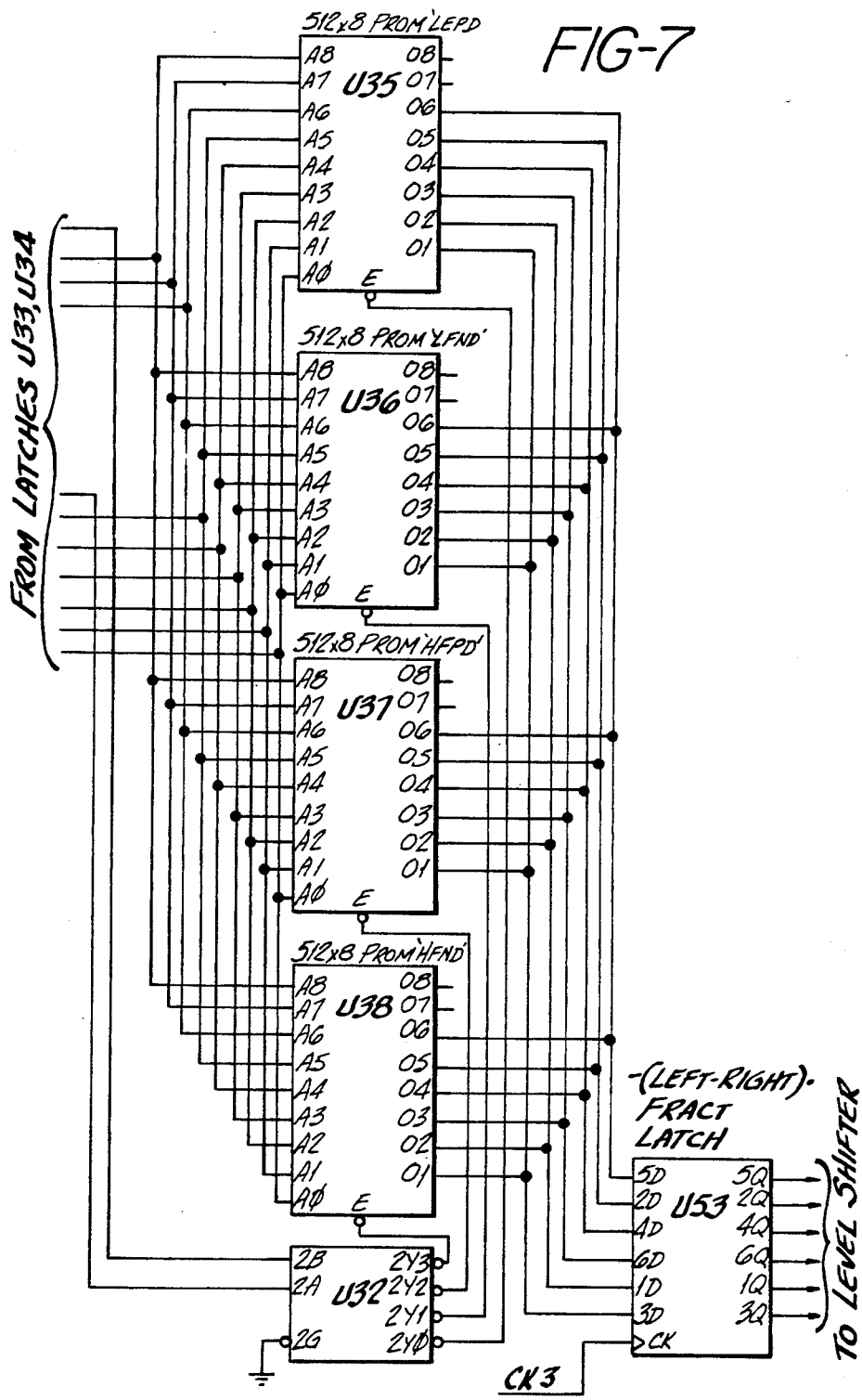
Figure 8:
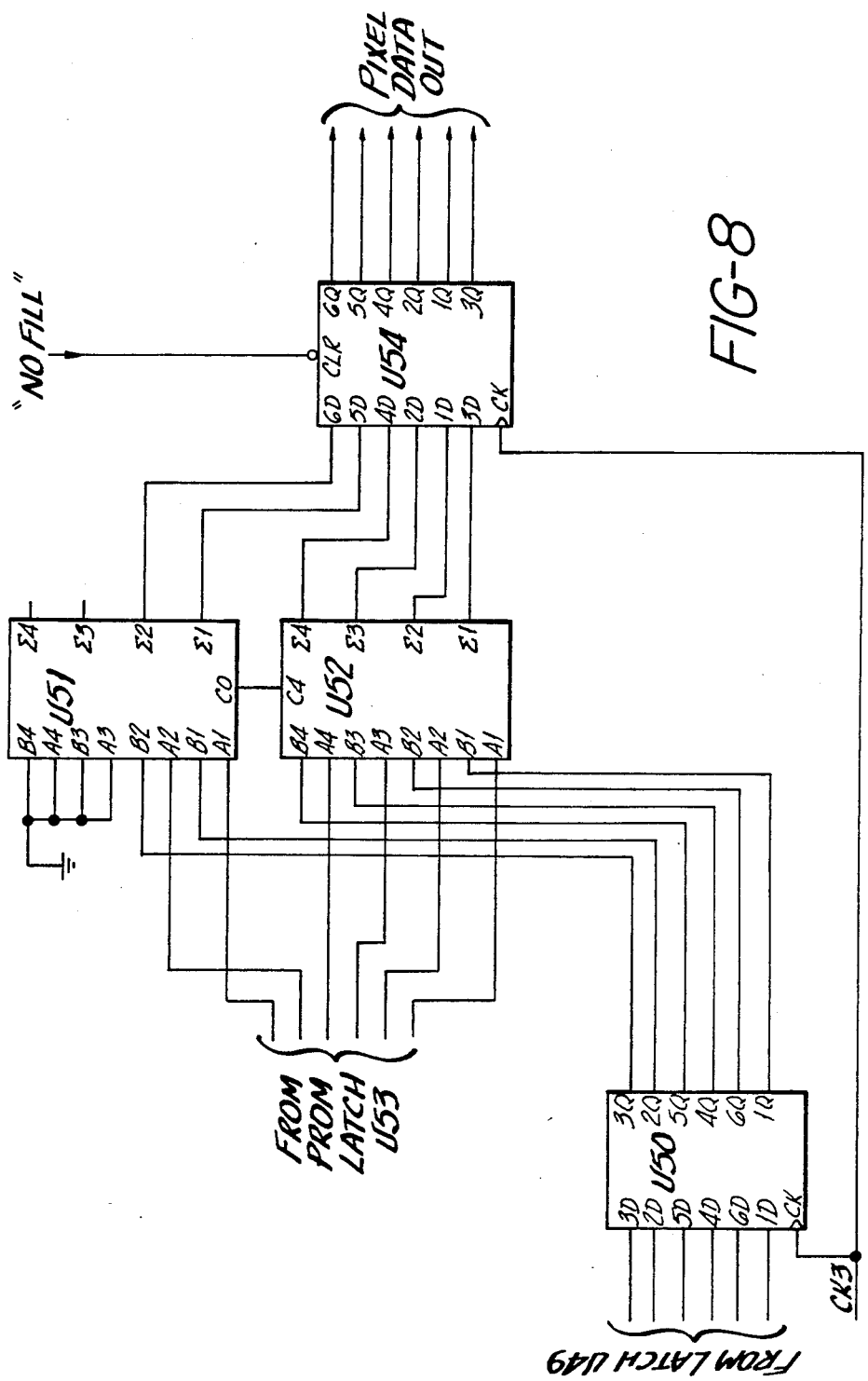
Figure 9:
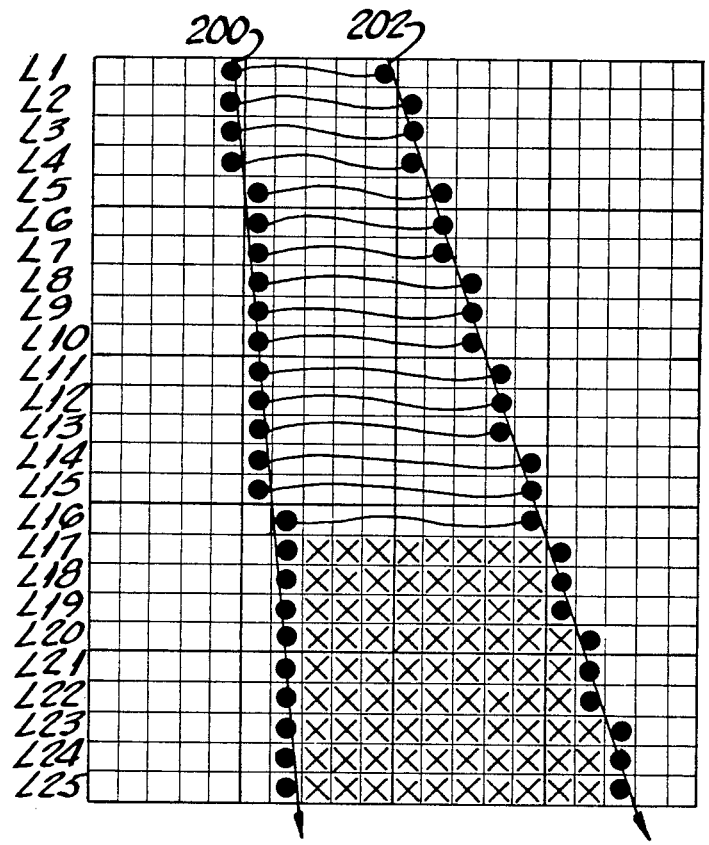

FIGS. 4A, 4B, 5A, and 5B illustrate in block diagram form circuitry which identifies the length of a sequence of hole pixels;

FIGS. 6 and 7 illustrate in block diagram form circuitry for producing interpolated pixel values;

FIG. 8 illustrates in block diagram form circuitry for shifting interpolated values to a desired level; and FIG. 9 represents a display of pixels illustrating the principles of the present invention.

In an ultrasonic diagnostic imaging system, an ultrasonic transducer sends beams or rays of ultrasonic energy into tissue which is being imaged. Interfaces within the tissue reflect some of this energy back to the transducer, which converts the echoes into electrical signals. These signals are coordinated with their times of occurrence to locate the positions of the tissue interfaces in the reproduced image. When a sector scanner is used for imaging, the echo information is organized in a R-$\theta$ format, where R is the distance from the transducer to the point from which the echo returned, and $\theta$ is the angle of the ray of ultrasonic energy which resulted in the echo relative to a reference angle. A scan converter receives the R-$\theta$ formatted information and digitally stores it in an x-y coordinate system of pixel values suitable for presentation as an x-y display. In a preferred embodiment of the present invention, the echo information is stored as six-bit pixels in a sequence of lines in the y-direction, with each line extending in the x-direction.

Figure 1:
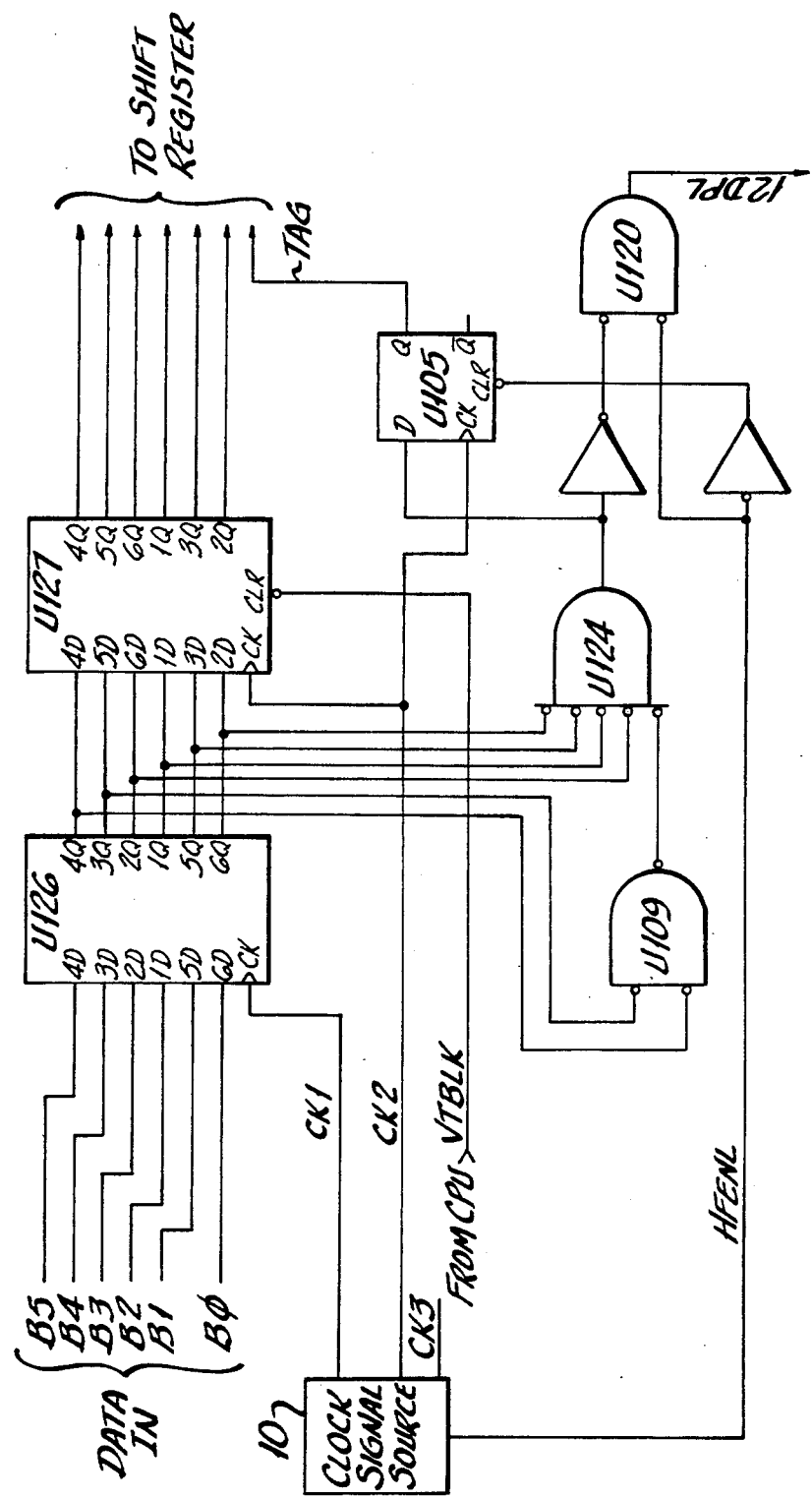
FIG. 1 illustrates in block diagram form circuitry for identifying and tagging hole pixels.

The lines of pixel values are clocked out of the scan converter, one line after another, and are examined to determine the existence of hole pixels, which are characterized by all zero bits. Referring to FIG. 1, pixel data bits B0-B5 are clocked into a six-bit latch U126 by a clock signal CK1. The latched data bits are applied to inputs of NAND gates U109 and U124 to determine if the bits are all zeroes. If an all zero bit word is present, a flip-flop U105 is set as the observed six-bit word is clocked into a latch U127. When the data word latched into U127 is a valid information signal (i.e., is not all zeroes), it is transferred to a shift register along with a zero value "TAG" bit from flip-flop U105. When the data word is all zeroes, a TAG bit value of "one" accompanies the zero value data word to the shift register. The pixel which is momentarily stored in latch U127 is the fourteenth pixel in a sequence of pixels, numbered zero through eleven plus LEP, stored temporarily in the shift register. The tag bit of the U127 pixel, 12DPL, is applied to the circuitry of FIG. 4A for determination of the length of a sequence of hole pixels.

The shift register which receives the data words and TAG bits, termed a "hole filler pipeline", is shown in FIGS. 2A and 2B. The pipeline includes thirteen latches U128-U80 which hold and shift thirteen sequential pixel words and their associated TAG bits. Output signals are available in parallel from each latch, including the TAG bits, twelve of which are shown at the lower right-hand corner of FIG. 2B, labelled DATL and 00DPL-10DPL.

The twelve TAG bits from the hole filler pipeline are applied to inputs of hole fill programmable array logic U68 shown in FIG. 7. The programmable array logic is effectively a controllable AND gate, in which control bits HS0H, HS1H, and HS2H select the number of inputs of the AND gate which are to be activated. For example, the control bits may select five inputs to be examined, such as those receiving signals 06DPL–10DPL. Whenever at least one of these inputs is receiving a zero value TAG bit, indicating that at least one of the five consecutive pixels represented contains valid information from the scanning apparatus, the array logic will produce no output signal. But when all "one" value TAG bits are received by the selected inputs, indicating that this sequence of five pixels contains only hole pixels, the array logic produces an output signal to reset flip-flop U92, the Q output of which then goes to a low state.

When flip-flop U92 is not set and hole pixels are occurring between valid data words in the selected pixel sequence, the arrangement of the present invention is designed to fill in the hole pixels with calculated data values. When any two valid scan data words are separated by hole pixels, they are referred to as "endpoint" pixels, with the first endpoint in time being the "left endpoint" and the second in time being the "right endpoint". The pixels are subsequently displayed in a left-to-right scanning and display sequence.

Figure 4A:
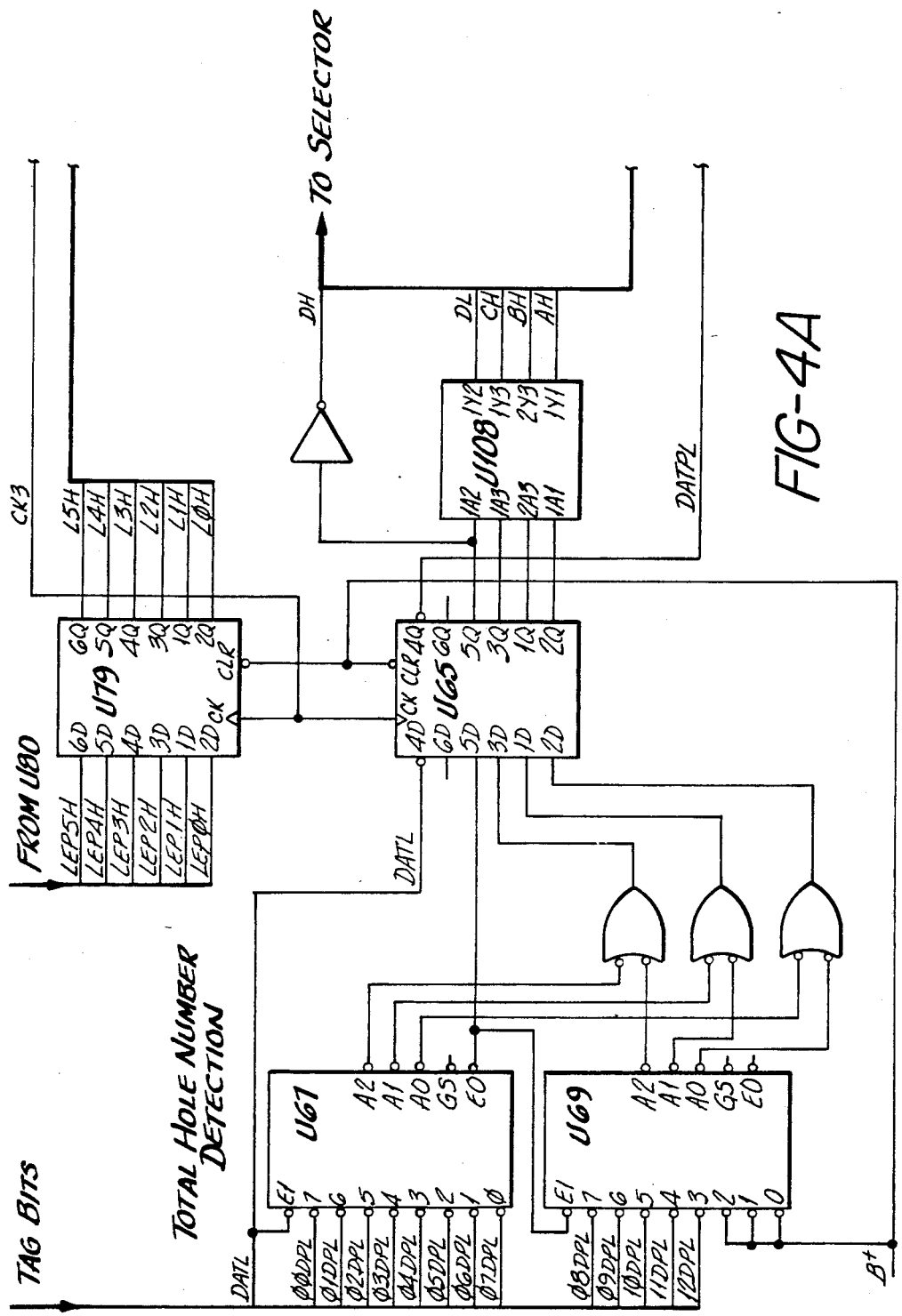
Figure 4B:
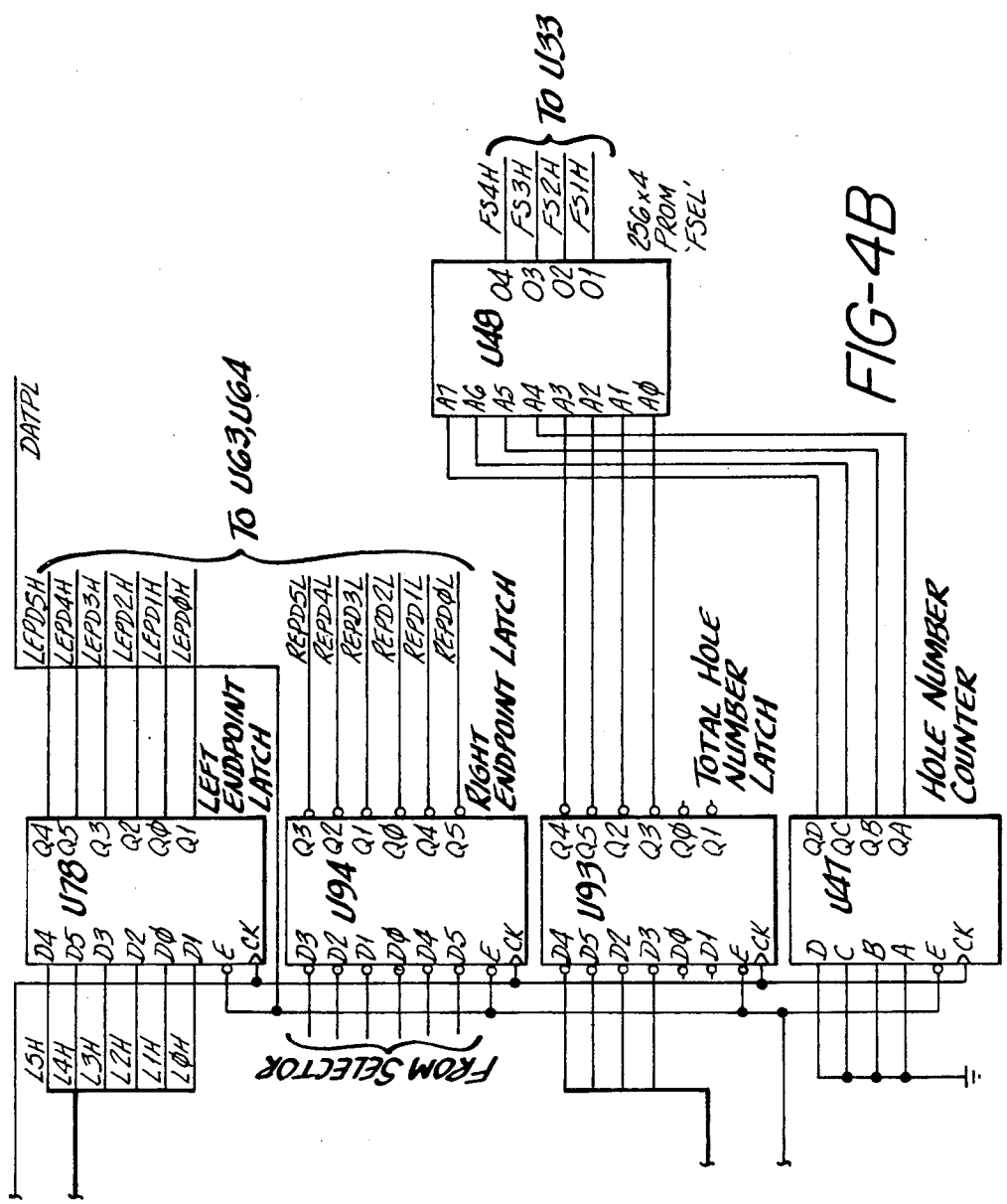

In FIG. 4A, decoders U67 and U69 receive the TAG bits from the pipeline of FIG. 2A–2B and produce code bits representative of the location of left and right endpoint pixels in the pipeline, and the number of intervening hole pixels. These code bits are latched into latch U65, from where they are transferred into a hole number register U93 in FIG. 4B. As the hole pixels are shifted through the pipeline a counter U47 counts them, and the outputs of devices U93 and U47 address a programmable read-only memory (PROM) U48, which generates a partial address for a hole fit PROM array to be described below. A code bit DATPL enables right and left endpoint latches U94 and U78 to store the left and right endpoint values. The left endpoint value is received from the last stage U80 of the pipeline, delayed by a latch stage U79, and is then latched into latch U78 when that latch is enabled by signal DATPL.

Figure 5A:
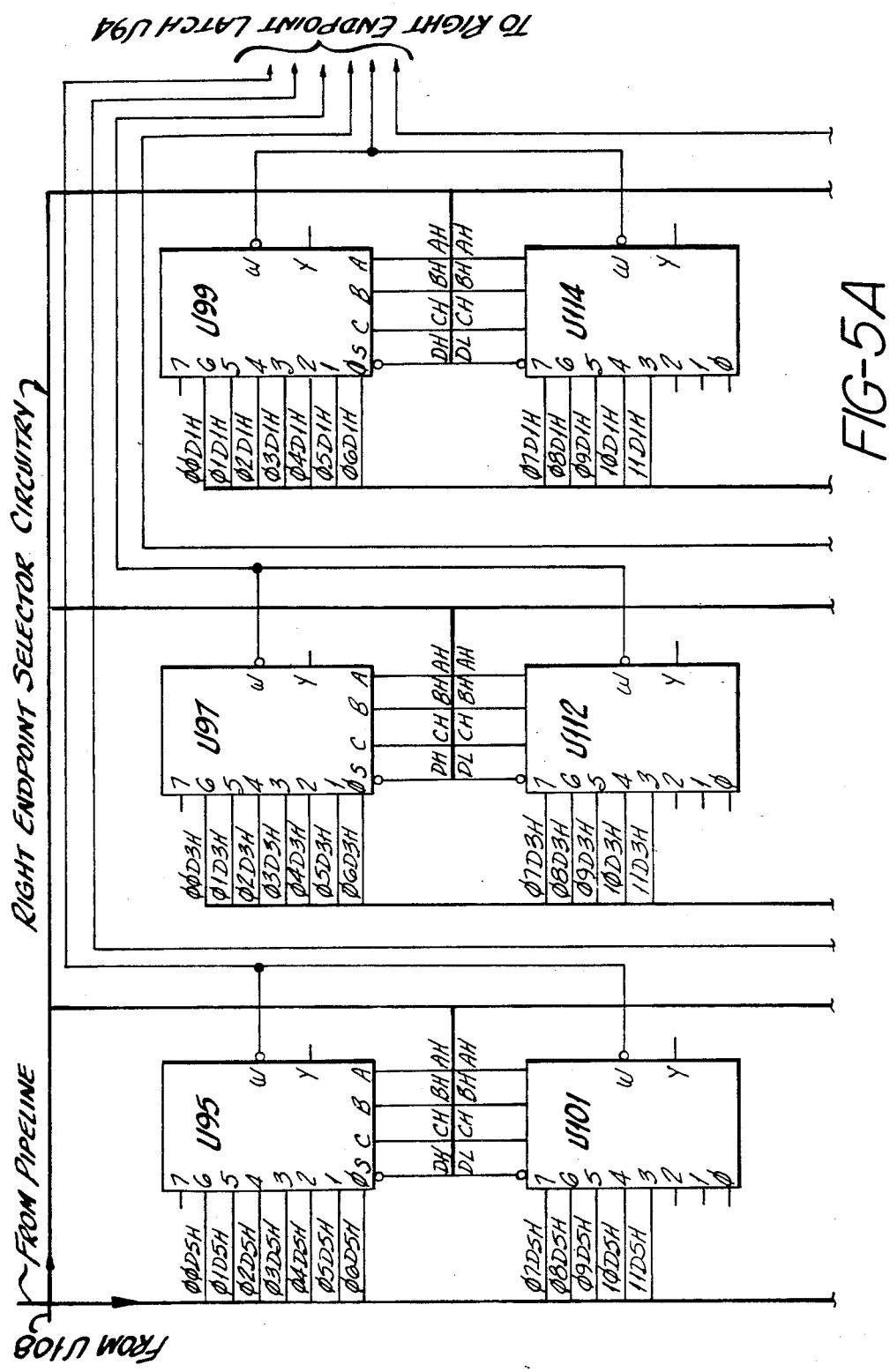
Figure 5B:
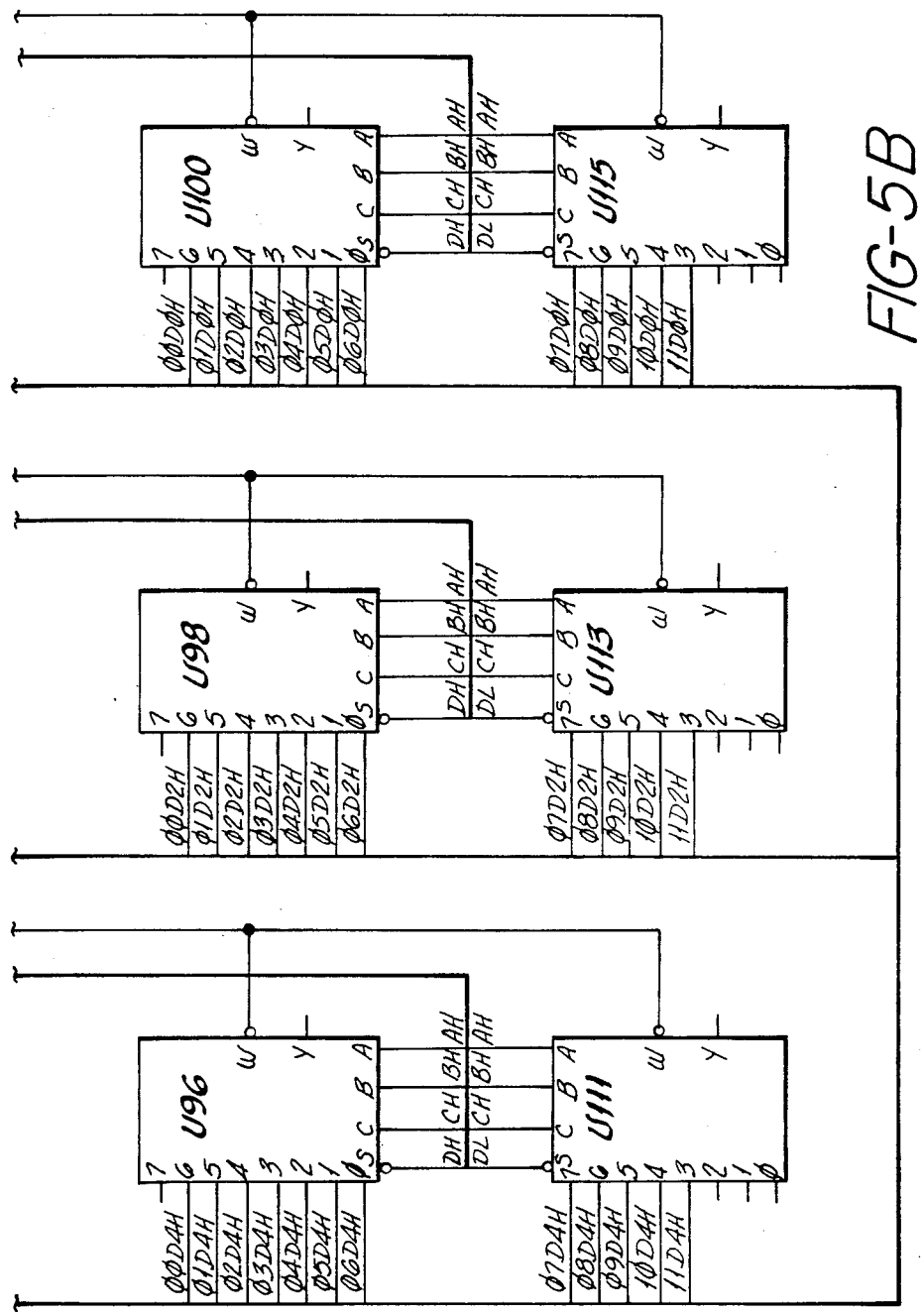

The code bits of latch U65 are applied by way of a buffer U108 to right endpoint selector circuitry, shown in FIGS. 5A and 5B, to continuously track the right endpoint through the pipeline. The parallel data bit outputs of the pipeline are coupled to the inputs of the selector circuitry, which comprise one-of-eight selector circuits. The code bits steer the bits of the tracked right endpoint pixel through the selector circuitry to the right endpoint latch U94.

The outputs of the right and left endpoint latches are applied to inputs of adder U63 and U64 of FIG. 6, where the endpoint values are subtractively combined to find the difference between them. The difference value is stored in left-right latch U34, and the partial address produced by PROM U48 is stored in latch U33. The outputs of latches U33 and U34 address the PROM array shown in FIG. 7, which produces calculated values of hole pixels between the two endpoints. The calculated pixel values are a function of the endpoint values, the length of the hole sequence between the endpoints, and the position of each hole pixel in the sequence, and may be determined by a stored Gaussian fit algorithm, for instance. The calculated pixel values are latched into a PROM output latch U53.

The calculated values held in latch U53 are normalized values, and are applied to inputs of adders U51 and U52 of FIG. 8, where the value of the left endpoint pixel is added to shift the data level. The left endpoint pixel value is applied to the adders by way of delay latches U49 and U50 to arrive at the adders in proper time sequence. The restored values from the adders are latched into an output latch U54, from which the pixel values are available for storage and/or display.

Figure 3:
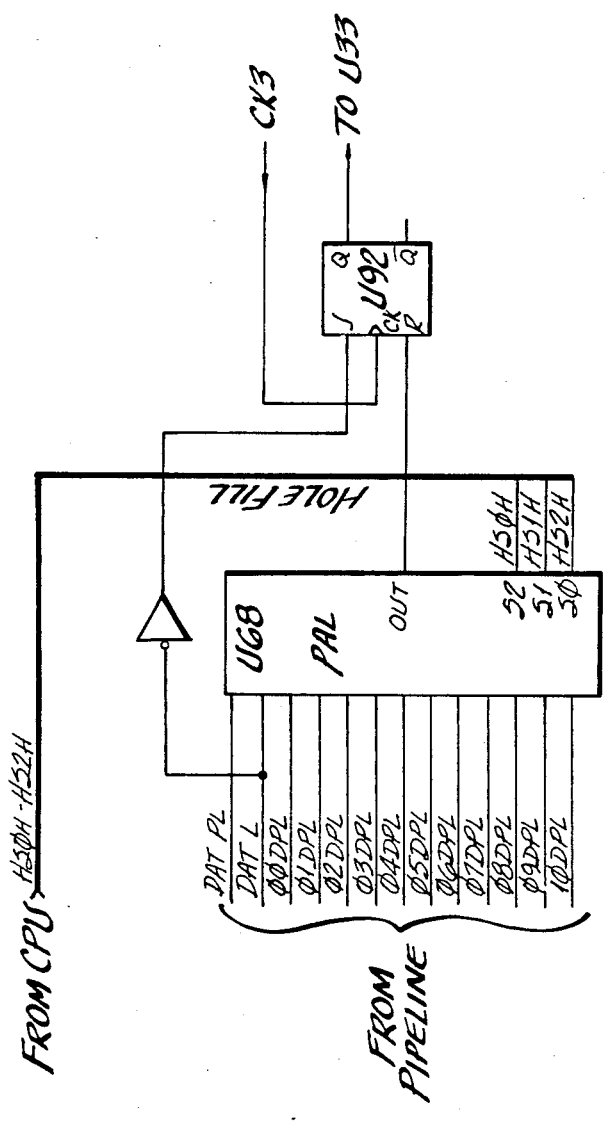
FIG. 3 illustrates in block diagram form a programmable array of logic which determines the length of a sequence of hole pixels to be filled in with interpolated values.

When the hole fill array logic of FIG. 3 detects a hole sequence which is too long to fill, the low signal at the output of flip-flop U92 is latched into latch U33 of FIG. 6. This low signal is delayed by latch U33 by a wraparound connection sequence so that a delayed signal "NO FILL" is produced at output 4Q of the latch when the long sequence is about to be loaded into output latch U54. The low "NO FILL" signal will then clear the contents of latch U54 of FIG. 8 during the long sequence, resulting in a blanking of that area of the displayed information.

The operation of the arrangement of FIGS. 1–8 is illustratively shown in FIG. 9. FIG. 9 represents a portion of an image display, in which each pixel is represented by a square. Overlaying the display are two ultrasonic beams 200 and 202 transmitted by either a sector scanner or B-scan probe. Each pixel which contains valid scan data from a scanning beam is filled in with a large dot. Thus, the column of dotted pixels resulting from scanning beam 200 represents left endpoint pixels and the column of dotted pixels resulting from scanning beam 202 represents right endpoint pixels for each line of pixels.

Assume that the control signals for the programmable array logic U68 in FIG. 3 are controlling the array to look for sequences of eight consecutive hole pixels. It may be seen that array U68 will produce no output signals between the endpoints for each of lines L1 through L16, since each hole sequence between respective endpoints is seven or fewer. Interpolated pixel valves will thus fill in the hole pixels in lines L1 through L16, as indicated by the curved lines between these endpoints.

But from line L17 through L25, the array will detect sequences of eight or more holes. During these hole sequences the array will produce an output signal, and the "NO FILL" command will blank these sequences, as represented by the "X's" in the pixel squares between the endpoints (dotted pixels) of lines L17 through L25.

When a sector scanner is providing display information, a coarse examination is generally being performed and the filling of relatively lengthy hole sequences (e.g., ten or twelve) is usually acceptable. However, when a B-scan examination is being performed, more detailed, precise information is generally required. Therefore, only relatively shorter hole sequences will be filled, with longer sequences being blanked by the system to indicate to the user that the information from these areas is not detailed enough to present a display of the desired accuracy.

What is claimed is:

1. In an ultrasonic diagnostic imaging system, including a source of ultrasonic vectors and a two-dimensional display for displaying ones of said vectors in substantially a y direction; apparatus for providing pixel information in substantially the x direction between data points of said vectors comprising:

means responsive to said source of vectors, for producing a sequence of pixel values in said x direction, including valid pixel values representative of said vector information separated by hole pixel values which are not representative of said vector information;

means for variably setting a maximal number of hole pixel values which are to be interpolated between valid pixel values;

means, responsive to said sequence of pixel values, for tagging pixel values as either valid or hole pixel values;

means, responsive to the tags of a sequence, for comparing the length of a sequence of hole pixel values between valid pixel values with said maximal number; and means, responsive to said comparing means, for filling in said hole pixel sequence with interpolated values when said sequence length is less than said maximal number, and for blanking said hole pixel sequence when said sequence length is greater than said maximal number.

2. The arrangement of claim 1, wherein said pixel values comprise digital words, said valid pixel values being non-zero digital words and said hole pixel values being zero-value digital words.

3. The arrangement of claim 2, wherein said hole filling means includes:

a shift register, having an input coupled to said tagging means, for shifting a sequence of pixels and their respective tags.

4. In an ultrasonic diagnostic imaging system, including a source of ultrasonic vectors and a two-dimensional display for displaying ones of said vectors in substantially a y direction; apparatus for providing pixel information in substantially the x direction between data points of said vectors comprising:

means responsive to said source of vectors, for producing a sequence of pixel values in said x direction, including valid pixel values representative of said vector information separated by hole pixel values which are not representative of said vector information;

means for setting a maximal number of hole pixel values which are to be interpolated between valid pixel values;

means, responsive to said sequence of pixel values, for tagging pixel values as either valid or hole pixel values;

means, responsive to the tags of a sequence, for comparing the length of a sequence of hole pixel values between valid pixel values with said maximal number; and means, responsive to said comparing means, for filling in said hole pixel sequence with interpolated values when said sequence length is less than said maximal number, and for blanking said hole pixel sequence when said sequence length is greater than said maximal number;

wherein said pixel values comprise digital words, said valid pixel values being non-zero digital words and said hole pixel values being zero-value digital words;

wherein said hole filling means includes:

a shift register, having an input coupled to said tagging means, for shifting a sequence of pixels and their respective tags; and wherein said comparing means comprises programmable array logic controlled by said maximal number setting means and producing an output signal when a selected sequence of hole pixel tags exceeds said maximal number;

wherein said output signal is applied to said hole filling means.

5. The arrangement of claim 4, wherein said hole filling means includes an output register which produces a sequence of interpolated pixel values for a sequence of holes which is less than said maximal number, and a sequence of zero value pixels in response to said output signal of said programmable array logic.

6. In an ultrasonic diagnostic imaging system, including a source of ultrasonic vectors and a two-dimensional display for displaying ones of said vectors in substantially a y direction; apparatus for providing pixel information in substantially the x direction between data points of said vectors comprising:

means responsive to said source of vectors, for producing a sequence of pixel values in said x direction, including valid pixel values representative of said vector information separated by hole pixel values which are not representative of said vector information;

means for setting a maximal number of hole pixel values which are to be interpolated between valid pixel values;

means, responsive to said sequence of pixel values, for tagging pixel values as either valid or hole pixel values;

means, responsive to the tags of a sequence, for comparing the length of a sequence of hole pixel values between valid pixel values with said maximal number; and means, responsive to said comparing means, for filling in said hole pixel sequence with interpolated values when said sequence length is less than said maximal number, and for blanking said hole pixel sequence when said sequence length is greater than said maximal number;

wherein said pixel values comprise digital words, said valid pixel values being non-zero digital words and said hole pixel values being zero-value digital words; and wherein said hole filling means includes:

means, responsive to a sequence of pixel values, for identifying valid pixel values which precede and succeed a sequence of hole pixel values;

an interpolator, responsive to said valid pixel values which precede and succeed a sequence of hole pixel values, for producing interpolated values for said sequence of hole pixel values; and an output register, responsive to said valid and interpolated pixel values, and coupled to said interpolator and said comparing means, and producing either said interpolated values or blanked values between said valid pixel values.

7. The arrangement of claim 6, further comprising a scan converter, having an input responsive to said ultrasonic vectors and an output coupled to said pixel sequence producing means, for storing said ultrasonic vectors in an x-y coordinate format.

8. In an ultrasonic diagnostic imaging system, including a source of ultrasonic vectors and a two-dimensional display for displaying ones of said vectors in substantially a y direction; apparatus for providing pixel information in substantially the x direction between data points of adjacent ones of said vectors comprising:

means responsive to said source of vectors, for producing a sequence of pixel values in said x direction, including valid pixel values representative of said vector information separated by hole pixel values which are not representative of said vector information;

means for variably setting a maximal number of hole pixel values which are to be interpolated between valid pixel values;

means, responsive to said sequence of pixel values, for identifying pixel values as either valid or hole pixel values;

means, responsive to said sequence of identified pixels, for comparing the length of a sequence of hole pixel values between valid pixel values with said maximal number; and means, responsive to said comparing means, for filling in said hole pixel sequence with interpolated values when said sequence length is less than said maximal number, and for blanking said hole pixel sequence when said sequence length is greater than said maximal number.

* * * * *